US011410350B2

(12) United States Patent
Nakanishi

(10) Patent No.: US 11,410,350 B2
(45) Date of Patent: Aug. 9, 2022

(54) MEDICAL IMAGE PROCESSING APPARATUS AND X-RAY CT APPARATUS

(71) Applicant: CANON MEDICAL SYSTEMS CORPORATION, Otawara (JP)

(72) Inventor: Satoru Nakanishi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 23 days.

(21) Appl. No.: 16/654,306

(22) Filed: Oct. 16, 2019

(65) Prior Publication Data

US 2020/0118308 A1 Apr. 16, 2020

(30) Foreign Application Priority Data

Oct. 16, 2018 (JP) .............................. JP2018-194875
Oct. 15, 2019 (JP) .............................. JP2019-188394

(51) Int. Cl.
*G06T 11/00* (2006.01)
*A61B 6/03* (2006.01)

(52) U.S. Cl.
CPC ............ *G06T 11/005* (2013.01); *A61B 6/032* (2013.01); *G06T 11/006* (2013.01); *G06T 11/008* (2013.01); *G06T 2210/41* (2013.01)

(58) Field of Classification Search
None
See application file for complete search history.

(56) References Cited

U.S. PATENT DOCUMENTS 9,202,296 B2 * 12/2015 Yang .................. G06K 9/00221
2007/0269000 A1 * 11/2007 Partain ................ A61B 6/4241
378/37

(Continued)

FOREIGN PATENT DOCUMENTS

JP 2015-29913 A 2/2015

OTHER PUBLICATIONS

Peters, T. (Mar. 10, 2016,). CT Image Reconstruction. Retrieved Mar. 18, 2021, from http://www.aapm.org/meetings/02am/pdf/8372-23331.pdf (Year: 2016).*

(Continued)

*Primary Examiner* — Vu Le
*Assistant Examiner* — Courtney Joan Nelson
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry acquires information on missing data based on first projection data obtained by scanning a subject. The processing circuitry generates second projection data by interpolating missing data in the first projection data based on the information on missing data. The processing circuitry generates a first reconstructed image by reconstructing the second projection data. The processing circuitry generates third projection data by performing forward projection on the first reconstructed image. The processing circuitry generates fourth projection data by updating the second projection data based on the third projection data. The processing circuitry generates a second reconstructed image based on the fourth projection data.

16 Claims, 8 Drawing Sheets

(56) References Cited

U.S. PATENT DOCUMENTS

2012/0308101 A1* 12/2012 Zeng ............... G06T 11/008
 382/131
2015/0036902 A1* 2/2015 Zamyatin ......... G06T 11/003
 382/131

OTHER PUBLICATIONS

Pengwei Wu et al 2015 Phys. Med. Biol. 60 8437 (Year: 2015).*

* cited by examiner

MEDICAL IMAGE PROCESSING APPARATUS AND X-RAY CT APPARATUS

CROSS-REFERENCE TO RELATED APPLICATIONS

This application is based upon and claims the benefit of priority from Japanese Patent Application No. 2018-194875, filed on Oct. 16, 2018; and Japanese Patent Application No. 2019-188394, filed on Oct. 15, 2019; the entire contents of which are incorporated herein by reference.

FIELD

Embodiments described herein relate generally to a medical image processing apparatus and an X-ray CT apparatus.

BACKGROUND

At the time of the imaging of an X-ray CT apparatus, there is a case where it is not possible to normally collect projection data due to the loss of view or ray level data caused by discharge of an X-ray tube, failure of an X-ray detector, a communication error of a data acquisition system (DAS), and the like.

When there is a data loss in projection data, since the image quality of a reconstructed image is degraded, data having a loss is interpolated by normal data in the vicinity of a data position with the loss in the related art.

However, when there is a wide range of data loss in the projection data, there is a case where it is not possible to prevent image quality degradation only by the interpolation with the neighboring normal data.

DETAILED DESCRIPTION

A medical image processing apparatus according to an embodiment includes processing circuitry. The processing circuitry acquires information on missing data based on first projection data obtained by scanning a subject. The processing circuitry generates second projection data by interpolating missing data in the first projection data based on the information on missing data. The processing circuitry generates a first reconstructed image by reconstructing the second projection data. The processing circuitry generates third projection data by performing forward projection on the first reconstructed image. The processing circuitry generates fourth projection data by updating the second projection data based on the third projection data. The processing circuitry generates a second reconstructed image based on the fourth projection data.

Hereinafter, with reference to the drawings, each embodiment of a medical image processing apparatus and an X-ray CT apparatus will be described. The embodiment is not limited to the following content. Furthermore, content described in one embodiment or modification example is also applied in principle to other embodiments or modification examples in the same manner.

Figure 1:
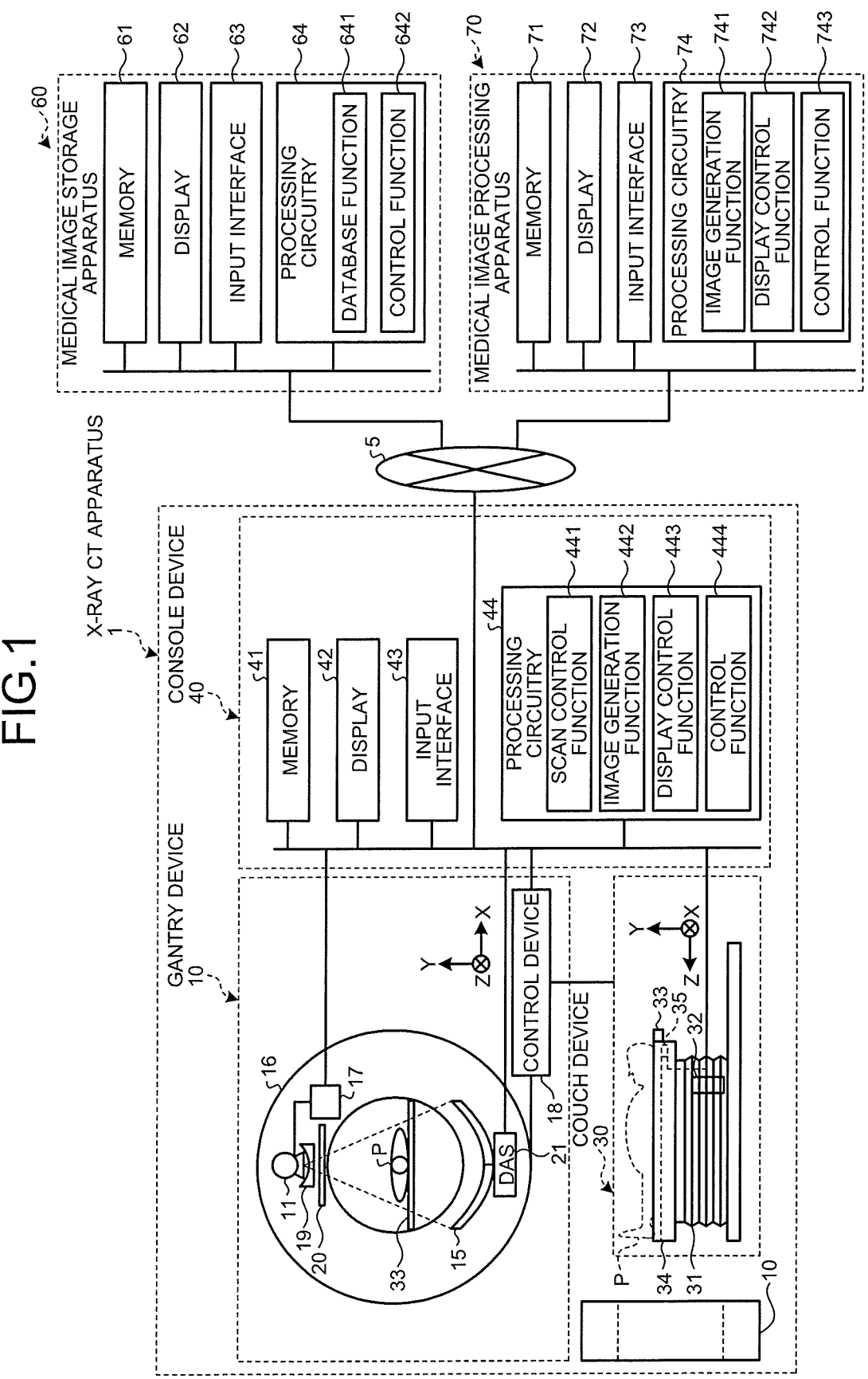
FIG. 1 is a block diagram illustrating a configuration example of an X-ray CT apparatus, a medical image storage apparatus, and a medical image processing apparatus according to an embodiment.

With reference to FIG. 1, a configuration of an X-ray CT apparatus 1 according to an embodiment will be described. FIG. 1 is a block diagram illustrating a configuration example of the X-ray CT apparatus 1, a medical image storage apparatus 60, and a medical image processing apparatus 70 according to an embodiment. In FIG. 1, the X-ray CT apparatus 1, the medical image storage apparatus 60, and the medical image processing apparatus 70 are communicably connected to one another via a communication network 5. When the X-ray CT apparatus 1 is used alone, the connection with the communication network 5 is not required and the medical image storage apparatus 60 and the medical image processing apparatus 70 are also not required. Furthermore, when processing on projection data and the like is performed in the medical image processing apparatus 70, a function corresponding to the processing can also be omitted from the X-ray CT apparatus 1.

The X-ray CT apparatus 1 includes a gantry device 10, a couch device 30, and a console device 40. For convenience of description, in FIG. 1, a plurality of gantry devices 10 are drawn; however, basically, there is one gantry device 10 as an actual configuration. In FIG. 1, it is assumed that the longitudinal direction of a rotating shaft of a rotating frame 16 or a couchtop 33 of the couch device 30 in a non-tilted state of the gantry device 10 is a Z axis direction. Furthermore, it is assumed that an axial direction orthogonal to the Z axis direction and horizontal to a floor surface is an X axis direction. Furthermore, it is assumed that an axial direction orthogonal to the Z axis direction and perpendicular to the floor surface is a Y axis direction.

The gantry device 10 includes an X-ray tube 11, an X-ray detector 15, the rotating frame 16, an X-ray high voltage device 17, a control device 18, a wedge 19, a collimator 20, and a data acquisition system (DAS) 21.

The X-ray tube 11 is a vacuum tube that generates X-rays by emitting thermoelectrons toward an anode (target) from a cathode (filament) with a high voltage from the X-ray high voltage device 17. For example, the X-ray tube 11 includes a rotating anode type X-ray tube that generates X-rays by emitting thermoelectrons to a rotating anode. The present embodiment can also be applied to a single tube type X-ray CT apparatus and what is called a multi-tube type X-ray CT apparatus in which a plurality of pairs of X-ray tubes and detectors are mounted on a rotating ring. Furthermore, hardware for generating X-rays is not limited to the X-ray tube 11. For example, instead of the X-ray tube 11, it may be possible to generate X-rays by using a $5^{th}$ generation method including a focus coil for collecting electron beams generated from an electron gun, a deflection coil for electromagnetically deflecting the electron beams, and a target ring for generating X-rays by a collision of the deflected electron beams surrounding the half circumference of a subject P.

The X-ray high voltage device 17 includes an electric circuitry such as a transformer and a rectifier, and includes a high voltage generation circuitry that generates a high voltage to be applied to the X-ray tube 11 and an X-ray control circuitry that controls an output voltage corresponding to the X-rays emitted by the X-ray tube 11. The high voltage generation device may be a transformer type device or an inverter type device. The X-ray high voltage device 17 performs the supply of power to the filament, the supply of driving power when the anode is a rotary type, and the like as well as the generation of the high voltage. Furthermore, the X-ray high voltage device 17 may be provided in the rotating frame 16, or may also be provided on a fixed frame (not illustrated) side of the gantry device 10. The fixed frame is a frame that rotatably supports the rotating frame 16.

The X-ray detector 15 detects the X-rays emitted from the X-ray tube 11 and passed through the subject P, and outputs a signal corresponding to the amount of the detected X-rays to the DAS 21. The X-ray detector 15, for example, includes a plurality of X-ray detection element arrays in which a plurality of X-ray detection elements are arranged in a channel direction (circumferential direction) along one arc centered on a focal point of the X-ray tube 11. The X-ray detector 15, for example, has a structure in which the X-ray detection element arrays in which the X-ray detection elements arranged in the channel direction are arranged in a slice direction (column direction and row direction).

Furthermore, the X-ray detector 15, for example, is an indirect conversion type detector including a grid, a scintillator array, and a photo sensor array. The scintillator array includes a plurality of scintillators, each of which includes a scintillator crystal that outputs light with a photon quantity corresponding to an incident X-ray dose. The grid is arranged on the surface of the scintillator array on an X-ray incident side and includes an X-ray blocking plate that absorbs scatted X-rays. The grid may also be referred to as a collimator (a one-dimensional collimator or a two-dimensional collimator). The photo sensor array has a function of converting light into electrical signals corresponding to the amount of light from the scintillator, and for example, includes photo sensors such as photodiodes and photomultiplier tubes (photomultipliers: PMT). The X-ray detector 15 may be a direct conversion type detector including a semiconductor element that converts the incident X-rays into electrical signals.

The rotating frame 16 (gantry base) is an annular frame that supports the X-ray tube 11 and the X-ray detector 15 opposite to each other and rotates the X-ray tube 11 and the X-ray detector 15 by the control device 18. For example, the rotating frame 16 is a casting made of aluminum. The rotating frame 16 can also support X-ray high voltage device 17 and the DAS 21 in addition to the X-ray tube 11 and the X-ray detector 15. Moreover, the rotating frame 16 can also support various constituents not illustrated in FIG. 1. Hereinafter, in the gantry device 10, a part, which rotationally moves with the rotating frame 16, and the rotating frame 16 are also referred to as a rotating part. So far, the rotate/rotate-type ($3^{rd}$ generation CT), in which the X-ray tube 11 and the X-ray detector 15 integrally rotate around the subject P, has been described. In addition, there are various types such as a stationary/rotate-type ($4^{th}$ generation CT) in which a plurality of X-ray detection elements arrayed in a ring shape are fixed and only the X-ray tube 11 rotates around the subject P, and any type can be applied to the present embodiment.

Detection data generated by the DAS 21 is transmitted from a transmitter provided in the rotating frame 16 and having a light emitting diode (LED) to a receiver provided in a non-rotating part of the gantry device 10 and having a photodiode, by optical communication, and is transmitted to the console device 40. The non-rotating part, for example, is the fixed frame (not illustrated in FIG. 1), which rotatably supports the rotating frame 16, and the like. The transmission method of the detection data from the rotating frame 16 to the non-rotating part of the gantry device 10 is not limited to the optical communication, and any method may be employed as long as data transmission can be performed between the rotating part and the non-rotating part.

The control device 18 includes a driving mechanism such as a motor and an actuator and circuitry that controls the mechanism. The control device 18 receives input signals from an input interface 43, an input interface provided in the gantry device 10, and the like and controls the operations of the gantry device 10 and the couch device 30. For example, the control device 18 controls the rotation of the rotating frame 16, the tilt of the gantry device 10, the operations of the couch device 30 and the couchtop 33, and the like. For example, as control for tilting the gantry device 10, the control device 18 rotates the rotating frame 16 around an axis parallel to the X axis direction based on information on an input inclination angle (tilt angle). The control device 18 may be provided in the gantry device 10 or may also be provided in the console device 40.

The wedge 19 is a filter for adjusting the dose of the X-rays emitted from the X-ray tube 11. Specifically, the wedge 19 is a filter that transmits and attenuates the X-rays emitted from the X-ray tube 11 such that the X-rays emitted to the subject P from the X-ray tube 11 have a predetermined distribution. For example, the wedge 19 is a wedge filter or a bow-tie filter and is configured by processing aluminum to have a predetermined target angle and a predetermined thickness.

The collimator 20 is a lead plate and the like for narrowing down the irradiation range of the X-rays having transmitted through the wedge 19 and forms a slit by a combination of a plurality of lead plates and the like. The collimator 20 is also referred to as an X-ray diaphragm. The opening degree and the position of the collimator 20 are adjusted by a collimator adjustment circuitry (not illustrated). In this way, the irradiation range of the X-rays generated by the X-ray tube 11 is adjusted.

The DAS 21 includes an amplifier that performs an amplification process on the electrical signals output from each X-ray detector element of the X-ray detector 15 and an A/D converter that converts the electrical signals to digital signals, and generates detection data. The DAS 21, for example, is implemented by a processor. The detection data generated by the DAS 21 is transmitted to the console device 40. Furthermore, the DAS 21 is an example of a data acquisition unit.

The couch device 30 is a device that places and moves the subject P to be scanned and includes a pedestal 31, a couch driving device 32, the couchtop 33, and a support frame 34. The pedestal 31 is a casing that supports the support frame 34 so as to be movable in a vertical direction. The couch driving device 32 is a driving mechanism that moves the couchtop 33, on which the subject P is placed, in a long axis direction of the couchtop 33 and includes a motor, an actuator, and the like. The couchtop 33 provided on the upper surface of the support frame 34 is a plate on which the subject P is placed. The couch driving device 32 may also move the support frame 34 in the long axis direction of the couchtop 33 in addition to the couchtop 33. Only the couchtop 33 may also be moved, or a method of moving together with the support frame of the couch device 30 may be used. When applied to upright CT, a method of moving a subject support mechanism corresponding to the couchtop 33 may be used. When performing a scan (helical scan, positioning scan, and the like) involving a relative change in positional relation between the gantry device 10 and the couchtop 33, the relative change in the positional relation may be performed by driving the couchtop 33, by running the gantry device 10, or by a combination thereof. When applied to dental CT, the couch device 30 and the like are not required.

The console device 40 includes a memory 41, a display 42, an input interface 43, and processing circuitry 44. Although the console device 40 is described as a separate body from the gantry device 10, the gantry device 10 may include the console device 40 or a part of constituent components of the console device 40.

The memory 41, for example, is implemented by a semiconductor memory element such as a random access memory (RAM) and a flash memory, a hard disk, an optical disk, and the like. For example, the memory 41 stores projection data and reconstructed image data. Furthermore, for example, the memory 41 stores computer programs required when circuitry included in the X-ray CT apparatus 1 performs its functions. The memory 41 is also used as a non-transitory storage medium by hardware. The storage of the projection data and the reconstructed image data is not limited to being performed by the memory 41 of the console device 40, and the medical image storage apparatus 60 such as a cloud server connectable to the X-ray CT apparatus 1 via the communication network 5 such as the Internet may store the projection data and the reconstructed image data in response to a storage request from the X-ray CT apparatus 1.

The display 42 displays various kinds of information. For example, the display 42 outputs a medical image (CT image) generated by the processing circuitry 44, a graphical user interface (GUI) for receiving various kinds of operations from an operator, and the like. For example, the display 42 is a liquid crystal display or a cathode ray tube (CRT) display. Furthermore, the display 42 may be provided in the gantry device 10. Furthermore, the display 42 may be a desktop type, or may be configured with a tablet terminal and the like that can wirelessly communicate with the body of the console device 40.

The input interface 43 receives various kinds of input operations from the operator, converts the received input operations into electrical signals, and outputs the electrical signals to the processing circuitry 44. For example, the input interface 43 receives, from the operator, a collection condition used when the projection data is collected, a reconstruction condition used when the CT image is reconstructed, an image processing condition used when a post-processing image is generated from the CT image data, and the like. For example, the input interface 43 is implemented by a mouse, a keyboard, a trackball, a switch, a button, a joystick, a touch panel, and the like. Furthermore, the input interface 43 may be provided in the gantry device 10. Furthermore, the input interface 43 may be configured with a tablet terminal and the like that can wirelessly communicate with the body of the console device 40.

The processing circuitry 44 controls the overall operation of the X-ray CT apparatus 1. For example, the processing circuitry 44 has a scan control function 441, an image generation function 442, a display control function 443, and a control function 444. The processing circuitry 44, for example, is implemented by a processor.

For example, the processing circuitry 44 reads a computer program corresponding to the scan control function 441 from the memory 41 and executes the read computer program, thereby controlling the X-ray CT apparatus 1 and performing a scan. The scan control function 441, for example, can perform a conventional scan, a helical scan, or a scan by various methods such as a step-and-shoot method.

Specifically, the scan control function 441 controls the couch driving device 32 to move the subject P into an imaging port of the gantry device 10. Furthermore, the scan control function 441 controls the X-ray high voltage device 17 to supply the X-ray tube 11 with a high voltage. Furthermore, the scan control function 441 adjusts the opening degree and the position of the collimator 20. Furthermore, the scan control function 441 controls the control device 18 to rotate the rotating part including the rotating frame 16. Furthermore, the scan control function 441 allows the DAS 21 to acquire projection data. In order to reconstruct the CT image, projection data for 360° corresponding to a circumference of the subject P is required, or projection data for 180°+fan angle is also required in a half scan. Any reconstruction method can be applied to the present embodiment.

Furthermore, for example, the processing circuitry 44 reads a computer program corresponding to the image generation function 442 from the memory 41 and executes the read computer program, thereby generating data obtained by performing pre-processing such as logarithmic transformation processing, offset correction processing, inter-channel sensitivity correction processing, and beam hardening correction on the detection data output from the DAS 21. Data (detection data) before the pre-processing and data after the pre-processing may be collectively referred to as projection data. Furthermore, for example, the image generation function 442 generates CT image data. Specifically, the image generation function 442 generates the CT image data by performing reconstruction processing using a filtered back projection method, a successive approximation reconstruction method, and the like on the projection data after the pre-processing. Furthermore, the image generation function 442 performs processing for improving image quality against image quality degradation due to missing data in the projection data. Details of the processing will be described below. Furthermore, based on the input operation received from the operator via the input interface 43, the image generation function 442 converts the CT image data into tomographic data or three-dimensional image data of an arbitrary section.

Furthermore, for example, the processing circuitry 44 reads a computer program corresponding to the display control function 443 from the memory 41 and executes the read computer program, thereby displaying the CT image on the display 42. Furthermore, for example, the processing circuitry 44 reads a computer program corresponding to the control function 444 from the memory 41 and executes the read computer program, thereby controlling various functions of the processing circuitry 44 based on the input operation received from the operator via the input interface 43.

Although FIG. 1 illustrates the case where the processing functions of the scan control function 441, the image generation function 442, the display control function 443, and the control function 444 are performed by the single processing circuitry 44, the embodiment is not limited thereto. For example, the processing circuitry 44 may be configured by combining a plurality of independent processors, or each processor may be configured to perform each processing function by executing each computer program. Furthermore, each processing function of the processing circuitry 44 may be performed by being appropriately distributed or integrated into a single processing circuit or a plurality of processing circuits. The processing circuitry 44 is not limited to being included in the console device 40 and may be included in an integrated server that collectively performs processing on detection data acquired by a plurality of medical image diagnosis apparatuses. Although the console device 40 has been described as performing a plurality of functions by a single console, the functions may be performed by separate consoles. Post-processing may be performed by any of the console device 40 and an external workstation. Alternatively, the post-processing may also be performed by both the console device 40 and the workstation.

On the other hand, the medical image storage apparatus 60 includes a memory 61, a display 62, an input interface 63, and processing circuitry 64. The processing circuitry 64 has a database function 641 and a control function 642.

The memory 61, for example, is implemented by a semiconductor memory element such as a random access memory (RAM) and a flash memory, a hard disk, an optical disk, and the like. For example, the memory 61 stores projection data and reconstructed image data. Furthermore, for example, the memory 61 stores computer programs required when circuitry included in the medical image storage apparatus 60 performs its functions. The memory 61 is also used as a non-transitory storage medium by hardware.

The display 62 displays various kinds of information. For example, the display 62 outputs a graphical user interface (GUI) for receiving various kinds of operations from the operator, and the like. For example, the display 62 is a liquid crystal display or a cathode ray tube (CRT) display.

The input interface 63 receives various kinds of input operations from the operator, converts the received input operations into electrical signals, and outputs the electrical signals to the processing circuitry 64. For example, the input interface 63 receives storage conditions and the like of a medical image from the operator. For example, the input interface 63 is implemented by a mouse, a keyboard, a trackball, a switch, a button, a joystick, a touch panel, and the like.

The processing circuitry 64 controls the overall operation of the medical image storage apparatus 60. For example, the processing circuitry 64 has the database function 641 and the control function 642. The processing circuitry 64, for example, is implemented by a processor.

For example, the processing circuitry 64 reads a computer program corresponding to the database function 641 from the memory 61 and executes the read computer program, thereby performing the input, storage, and output of the medical image.

Furthermore, for example, the processing circuitry 64 reads a computer program corresponding to the control function 642 from the memory 61 and executes the read computer program, thereby controlling various functions of the processing circuitry 64 based on the input operation received from the operator via the input interface 63.

Although FIG. 1 illustrates the case where the processing functions of the database function 641 and the control function 642 are performed by the single processing circuitry 64, the embodiment is not limited thereto. For example, the processing circuitry 64 may be configured by combining a plurality of independent processors, or each processor may be configured to perform each processing function by executing each computer program. Furthermore, each processing function of the processing circuitry 64 may be performed by being appropriately distributed or integrated into a single processing circuit or a plurality of processing circuits.

On the other hand, the medical image processing apparatus 70 includes a memory 71, a display 72, an input interface 73, and processing circuitry 74. The processing circuitry 74 has an image generation function 741, a display control function 742, and a control function 743.

The memory 71, for example, is implemented by a semiconductor memory element such as a random access memory (RAM) and a flash memory, a hard disk, an optical disk, and the like. For example, the memory 71 stores projection data and reconstructed image data. Furthermore, for example, the memory 71 stores computer programs required when circuitry included in the medical image processing apparatus 70 performs its functions. The memory 71 is also used as a non-transitory storage medium by hardware. The projection data and the reconstructed image data are acquired directly from the X-ray CT apparatus 1 or acquired via the medical image storage apparatus 60. Although it is assumed that the projection data is acquired in a state in which pre-processing has been completed, the projection data may be acquired in a state in which the pre-processing has not been completed. When the pre-processing has not been completed, the pre-processing is performed on the medical image processing apparatus 70 side.

The display 72 displays various kinds of information. For example, the display 72 outputs a medical image (CT image) generated by the processing circuitry 74, a graphical user interface (GUI) for receiving various kinds of operations from the operator, and the like. For example, the display 72 is a liquid crystal display or a cathode ray tube (CRT) display.

The input interface 73 receives various kinds of input operations from the operator, converts the received input operations into electrical signals, and outputs the electrical signals to the processing circuitry 74. For example, the input interface 73 receives, from the operator, a reconstruction condition used when the CT image is reconstructed, an image processing condition used when a post-processing image is generated from the CT image, and the like. For example, the input interface 73 is implemented by a mouse, a keyboard, a trackball, a switch, a button, a joystick, a touch panel, and the like.

The processing circuitry 74 controls the overall operation of the medical image processing apparatus 70. For example, the processing circuitry 74 has the image generation function 741, the display control function 742, and the control function 743. The processing circuitry 74, for example, is implemented by a processor.

For example, the processing circuitry 74 reads a computer program corresponding to the image generation function 741 from the memory 71 and executes the read computer program, thereby generating CT image data. Furthermore, when generating the CT image data, the image generation function 741 performs processing for improving image quality against image quality degradation due to missing data in the projection data. Details of the processing will be described below. Furthermore, based on the input operation received from the operator via the input interface 73, the image generation function 741 converts the CT image data into tomographic data or three-dimensional image data of an arbitrary section.

Furthermore, for example, the processing circuitry 74 reads a computer program corresponding to the display control function 742 from the memory 71 and executes the read computer program, thereby displaying the CT image on the display 72. Furthermore, for example, the processing circuitry 74 reads a computer program corresponding to the control function 743 from the memory 71 and executes the read computer program, thereby controlling various functions of the processing circuitry 74 based on the input operation received from the operator via the input interface 73.

Although FIG. 1 illustrates the case where the image generation function 741, the display control function 742, and the control function 743 are performed by the single processing circuitry 74, the embodiment is not limited thereto. For example, the processing circuitry 74 may be configured by combining a plurality of independent processors, or each processor may be configured to perform each processing function by executing each computer program. Furthermore, each processing function of the processing circuitry 74 may be performed by being appropriately distributed or integrated into a single processing circuit or a plurality of processing circuits.

The term "processor" used in the above description, for example, means circuitry such as a central processing unit (CPU), a graphics processing unit (GPU), an application specific integrated circuit (ASIC), a programmable logic device (for example, a simple programmable logic device (SPLD)), a complex programmable logic device (CPLD), or a field programmable gate array (FPGA). The processor performs functions by reading and executing the computer programs stored in the memories 41, 61, and 71. Instead of storing the computer programs in the memories 41, 61, and 71, the computer programs may be directly incorporated in the circuitry of the processor. In such a case, the processor performs the functions by reading and executing the computer programs incorporated in the circuitry. Each processor of the present embodiment is not limited to being configured as a single circuitry for each processor; However, one processor may be configured by combining a plurality of independent circuits to perform functions thereof.

Figure 2:
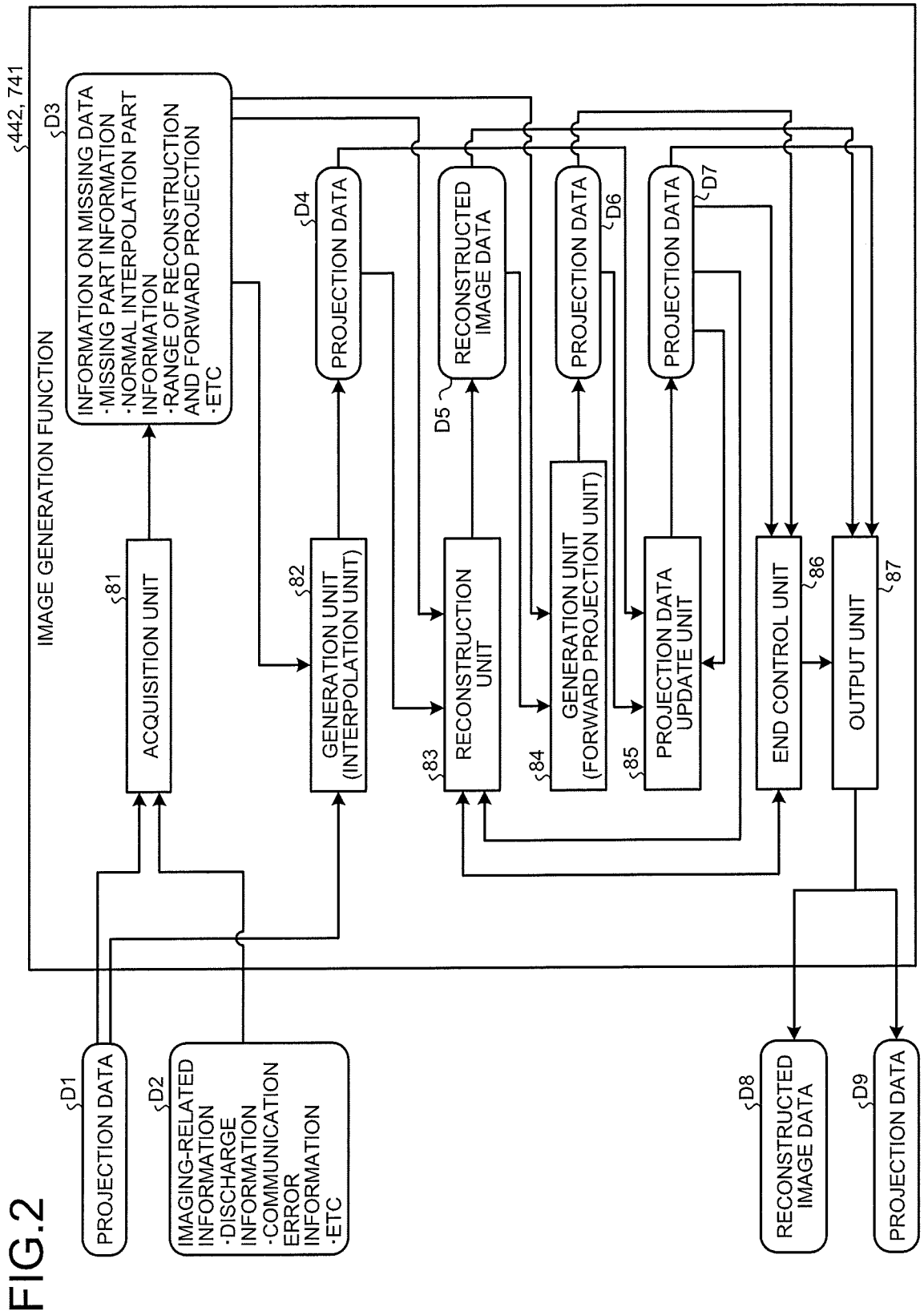
FIG. 2 is a block diagram illustrating a configuration example of an image generation function in processing circuitry.

FIG. 2 is a block diagram illustrating a configuration example of the image generation functions 442 and 741 in the processing circuitry 44 and the processing circuitry 74, and illustrates a configuration example for the processing for improving image quality against image quality degradation due to missing data in the projection data. In FIG. 2, the image generation functions 442 and 741 include an acquisition unit 81, a generation unit (interpolation unit) 82, a reconstruction unit 83, a generation unit (forward projection unit) 84, a projection data update unit 85, an end control unit 86, and an output unit 87.

The acquisition unit 81 has a function of receiving projection data D1 and imaging-related information D2, which are generated when the X-ray CT apparatus 1 scans the subject P and acquiring information D3 on missing data. The projection data D1 and the imaging-related information D2 are examples of first projection data. The imaging-related information D2 includes discharge information, communication error information, and the like. The discharge information is information on the discharge of the X-ray tube 11. The communication error information is information on a communication error between the DAS 21 and the processing circuitry 44 on the console device 40 side. In addition, there is information on failure of the X-ray detector 15. These pieces of information are recorded in correlation with events and generation times, for example.

The information D3 on missing data includes missing part information, normal interpolation part information, a range of reconstruction and forward projection, and the like. The missing part information is information indicating the position of missing data included in the projection data D1. The position of the data is represented by a channel (ch), a slice (sl), view, and the like. The normal interpolation part information is information indicating the position of normal data available for interpolating the missing data. The range of reconstruction and forward projection is information on the range of reconstruction and forward projection that are performed for the processing for improving image quality against image quality degradation due to missing data in the projection data. That is, since it is sufficient for the reconstruction and forward projection performed for the processing for improving image quality to have a range that affects the missing data, processing time can be shortened by limiting the range of a processing target.

The generation unit 82 has a function of generating interpolated projection data D4 by interpolating a missing data part of the projection data D1 based on the missing part information and the normal interpolation part information of the information D3 on missing data. The generation unit 82 is an example of a first generation unit. The projection data D4 is an example of second projection data.

The reconstruction unit 83 has a function of generating reconstructed image data D5 by performing reconstruction (backward projection) from the projection data D4 based on the range of reconstruction of the information D3 on missing data. Furthermore, the reconstruction unit 83 has a function of generating the reconstructed image data D5 by performing reconstruction from projection data D7 to be described below based on the range of reconstruction of the information D3 on missing data. The reconstructed image data D5 is an example of a first reconstructed image or a second reconstructed image.

The generation unit 84 has a function of generating projection data D6 by performing forward projection from the reconstructed image data D5 based on the range of forward projection of the information D3 on missing data. The generation unit 84 is an example of a second generation unit. The projection data D6 is an example of third projection data.

The projection data update unit 85 has a function of generating updated projection data D7 from the projection data D4 and the projection data D6. After the projection data D7 is generated, previous projection data D7 may be used for updating. The projection data update unit 85 is an example of a third generation unit. The projection data D7 is an example of fourth projection data.

The end control unit 86 has a function of determining whether to repeat or end processing following the reconstruction for improving image quality by the reconstruction unit 83 and controlling the processing. When it is determined to repeat the processing following the reconstruction for improving image quality by the reconstruction unit 83, the end control unit 86 allows the reconstruction unit 83 to repeat the processing following the reconstruction for improving image quality. Furthermore, when it is determined to end the processing, the end control unit 86 allows the reconstruction unit 83 to perform reconstruction for output. In relation to the determination regarding whether to repeat or end the reconstruction, it can be determined to end the reconstruction not only when a preset number of repetitions are performed (in the case of 1, the reconstruction is performed only once and is not repeated), but also when a difference between the projection data D6 and the projection data D7 from the previous time becomes less than a predetermined threshold value and the value is converged.

The image quality of the reconstructed image data D5, which is obtained by the reconstruction from the projection data D4 obtained by interpolating the projection data D1 included in the missing data, is improved as compared with a case where the reconstruction is performed from the projection data D1 in a state where no interpolation has been performed. However, since the reconstructed image data D5 is an image reconstructed from the state where the data has been interpolated in a cut-and-paste manner, it becomes an unnatural image. In this regard, in the present embodiment, the projection data D6 is further generated by the forward projection from the reconstructed image data D5, the latest projection data D4 and the like are updated by the projection data D6, this update is repeated as necessary, and finally the reconstructed image data D5 is acquired from the projection data D7, so that a high-quality reconstructed image without unnaturalness is obtained.

The output unit 87 has a function of outputting the final reconstructed image data D5, which has been generated by the reconstruction for output, as reconstructed image data D8 and outputting the latest projection data D7, which is the basis thereof, as projection data D9.

Figure 3:
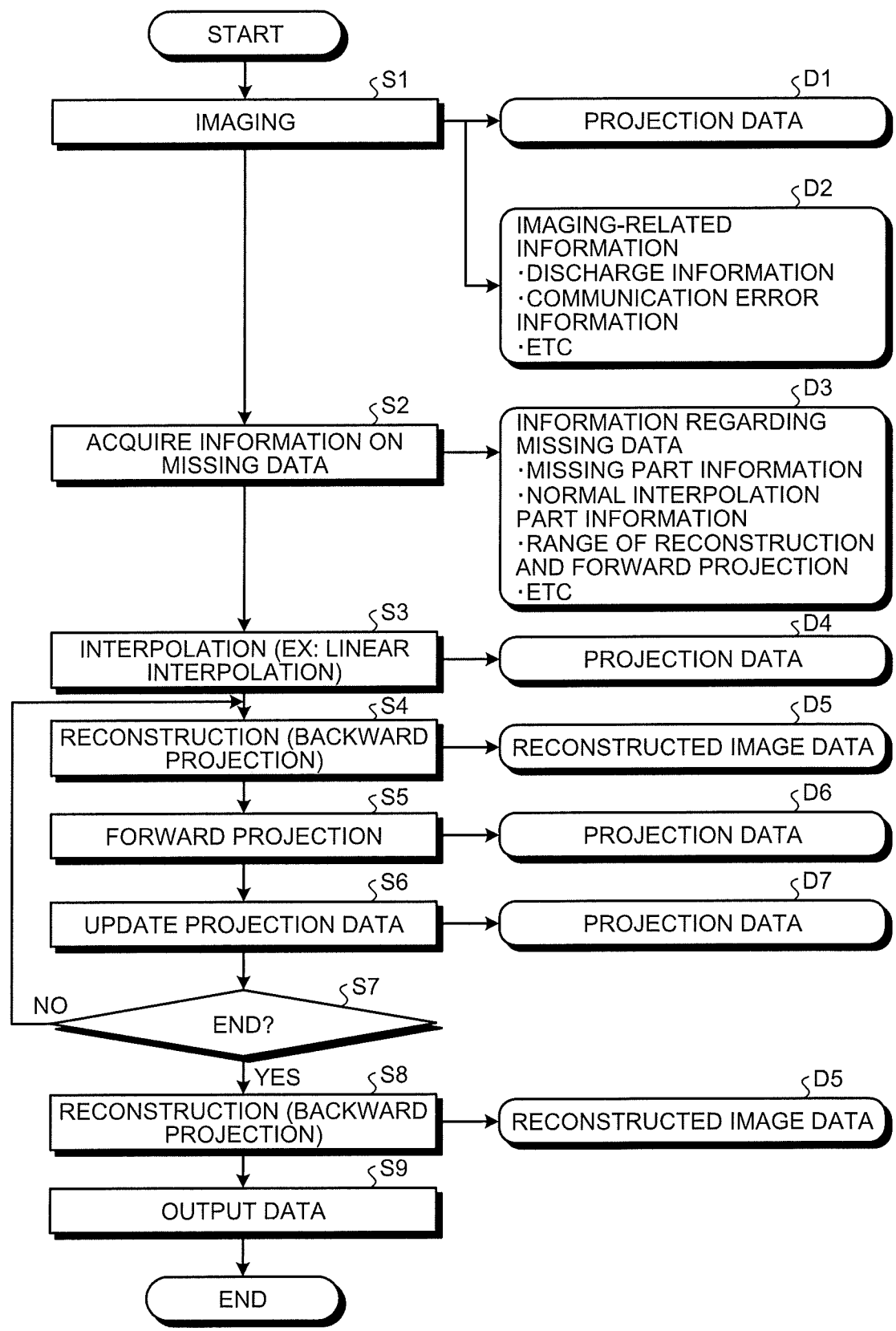
FIG. 3 is a flowchart illustrating a processing example of an embodiment.

FIG. 3 is a flowchart illustrating a processing example of the embodiment. In FIG. 3, when the subject P is imaged (scanned) by the scan control function 441 of the processing circuitry 44 of the X-ray CT apparatus 1 (step S1), the projection data D1 and the imaging-related information D2 are generated.

Next, the acquisition unit 81 of the image generation function 442 of the X-ray CT apparatus 1 or the image generation function 741 of the medical image processing apparatus 70 receives the projection data D1 and the imaging-related information D2 generated when the subject P is scanned and acquires the information D3 on missing data (step S2). The acquisition unit 81 specifies the position of the missing data based on the discharge information of the imaging-related information D2, the failure information of the X-ray detector, the communication error information, and the like with respect to the missing part information of the information D3 on missing data. The acquisition unit 81 may also specify the position of the missing data because the data includes an abnormal value.

Furthermore, when there is the loss of a ray level with respect to the normal interpolation part information, the acquisition unit 81, for example, specifies normal data of a channel or a slice adjacent to the channel of missing data in the same view or normal data of a channel corresponding to a view adjacent on a slice. Furthermore, when there is the loss of a view level, the acquisition unit 81, for example, specifies normal data of a view adjacent to the view of missing data or normal data of a view adjacent on a slice.

Figure 4A:
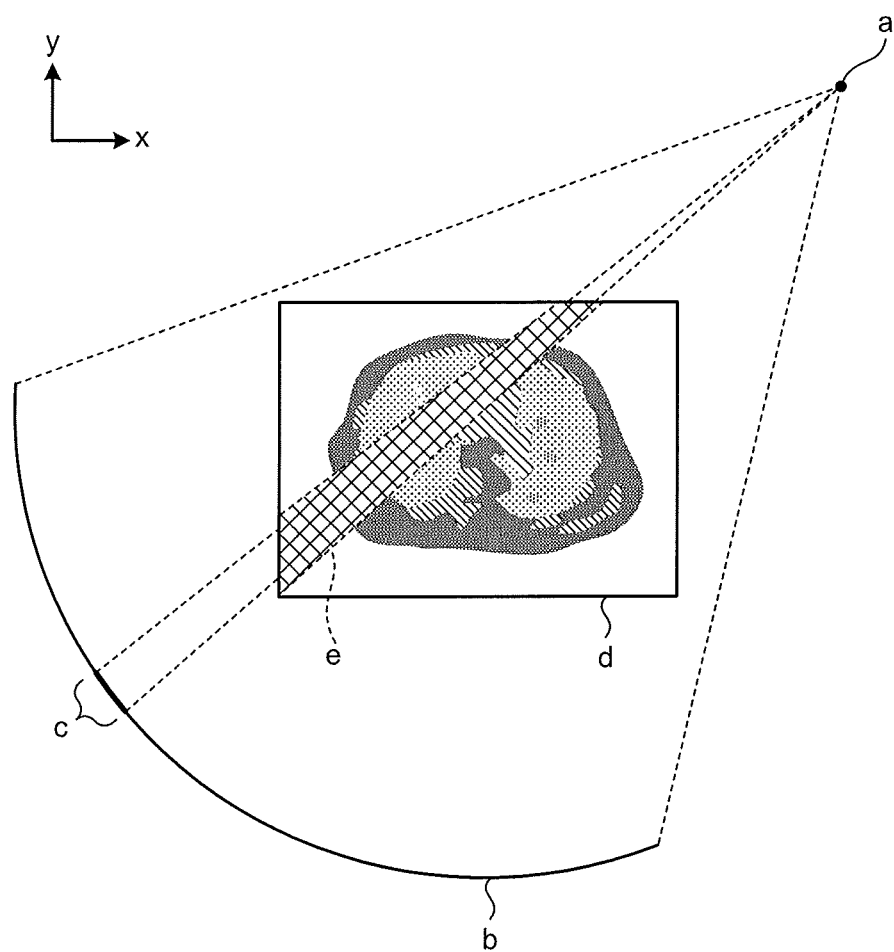
FIG. 4A is a diagram illustrating an example of a range of reconstruction for the loss of rays.
Figure 4B:
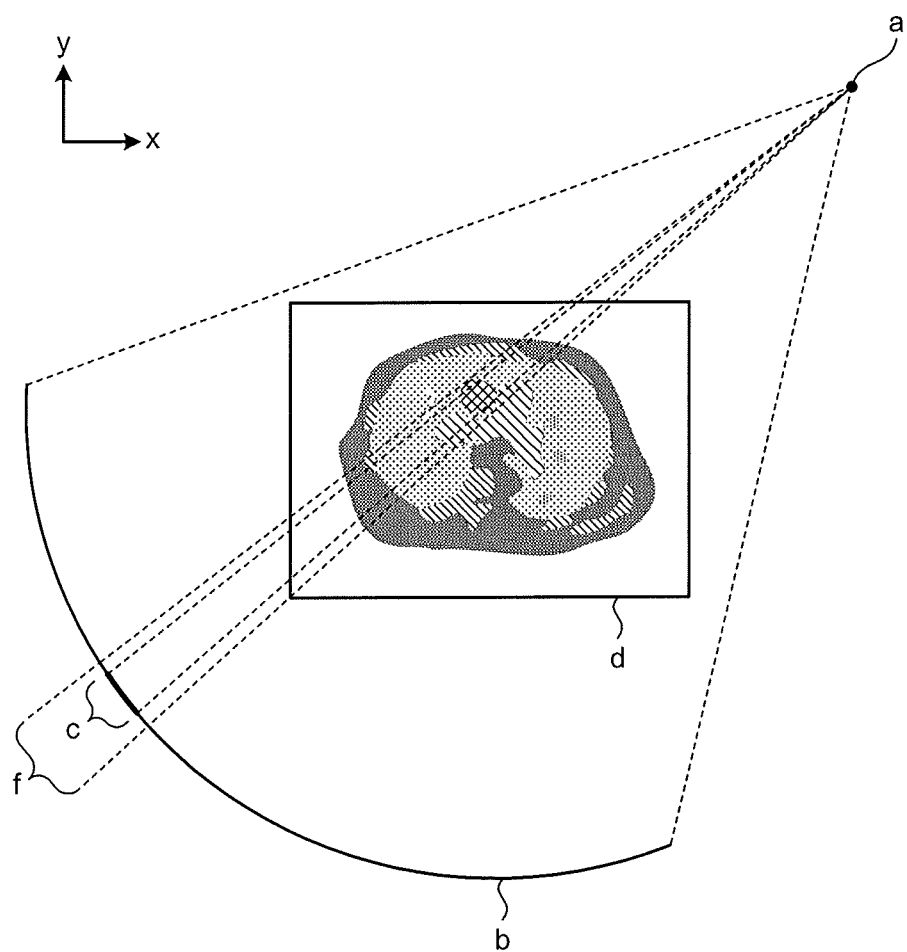
FIG. 4B is a diagram illustrating an example of a range of forward projection for the loss of rays.

Furthermore, with respect to the range of reconstruction and forward projection, the acquisition unit 81 specifies the range of reconstruction and the range of forward projection based on the position of the missing data in the projection data. FIG. 4A is a diagram illustrating an example of the range of reconstruction for the loss of rays. In FIG. 4A, when missing data c exists in a part of projection data b acquired by X-rays emitted from an X-ray source a, a range e that covers the missing data c in a reconstructed image d corresponding to a subject may be set as the range of reconstruction. Furthermore, FIG. 4B is a diagram illustrating an example of the range of forward projection for the loss of the rays. In FIG. 4B, when the missing data c exists in a part of the projection data b acquired by the X-rays emitted from the X-ray source a, a range f that covers the missing data c may be set as the range of forward projection.

Figure 5A:
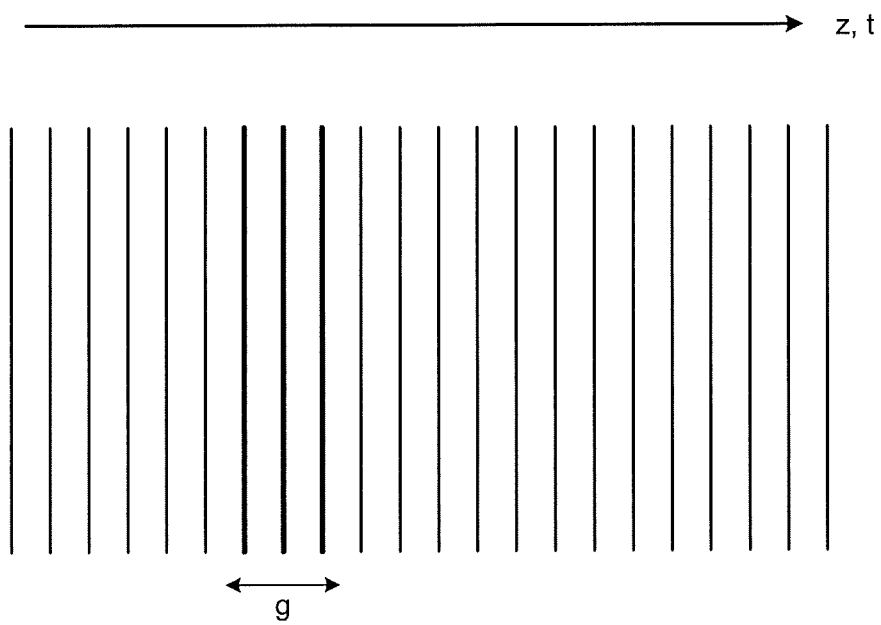
FIG. 5A is a first diagram illustrating an example of a range of reconstruction and forward projection for the loss of view.
Figure 5B:
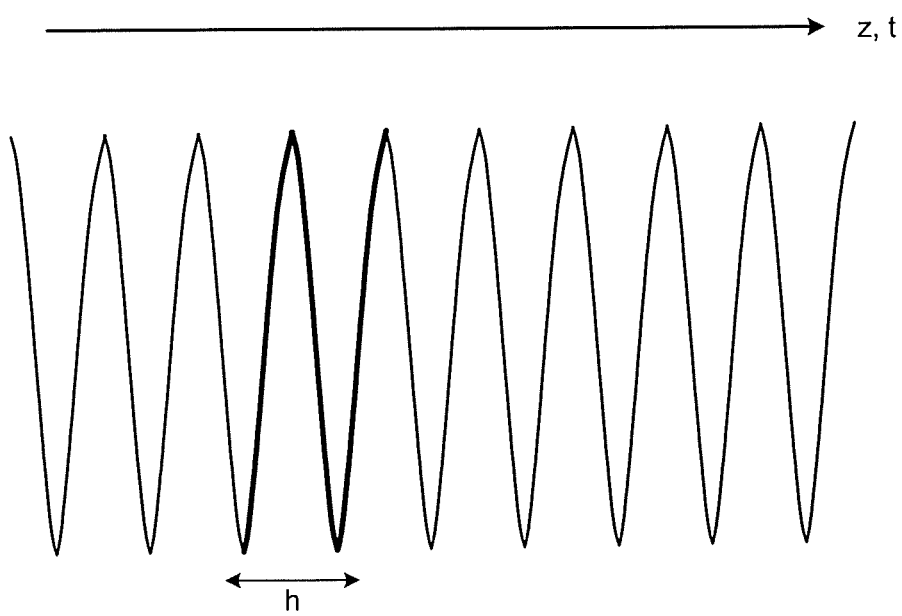
FIG. 5B is a second diagram illustrating an example of a range of reconstruction and forward projection for the loss of view.

FIG. 5A is a diagram illustrating an example of the range of reconstruction and forward projection for the loss of view, and illustrates a case where the loss of view has occurred in a range g when a plurality of slices are scanned by a step-and-shoot method. In such a case, the acquisition unit 81 sets the range g or a wider range including the range g as the range of reconstruction. Furthermore, FIG. 5B is a diagram illustrating another example of the range of reconstruction and forward projection for the loss of the view, and illustrates a case where the loss of view has occurred in a range h when a helical scan is performed. In such a case, the acquisition unit 81 sets the range h or a wider range including the range h as the range of reconstruction.

Returning back to FIG. 3, the generation unit 82 of the image generation function 442 of the X-ray CT apparatus 1 or the image generation function 741 of the medical image processing apparatus 70 generates the interpolated projection data D4 by interpolating the missing data part of the projection data D1 based on the missing part information and the normal interpolation part information of the information D3 on missing data (step S3).

Next, the reconstruction unit 83 of the image generation function 442 of the X-ray CT apparatus 1 or the image generation function 741 of the medical image processing apparatus 70 generates the reconstructed image data D5 by performing reconstruction (backward projection) from the projection data D4 based on the range of reconstruction of the information D3 on missing data (step S4).

Next, the generation unit 84 of the image generation function 442 of the X-ray CT apparatus 1 or the image generation function 741 of the medical image processing apparatus 70 generates the projection data D6 by performing forward projection from the reconstructed image data D5 based on the range of forward projection of the information D3 on missing data (step S5).

Next, the projection data update unit 85 of the image generation function 442 of the X-ray CT apparatus 1 or the image generation function 741 of the medical image processing apparatus 70 generates the updated projection data D7 from the projection data D4 and the projection data D6 (step S6). After the projection data D7 is generated, previous projection data D7 may be used for updating.

When the projection data D4 estimated by the interpolation is set as LI (ch, sl, view) and the projection data D6 obtained by $n^{th}$ forward projection is set as FPJ (ch, sl, view, n), then the $n^{th}$ updated projection data D7 (denoted as eproj) for example, is represented by:

$$eproj(ch, sl, view, n) = LI(ch, sl, view)*(1.0-w(n)) + FPJ(ch, sl, view, n)*w(n).$$

In the above, ch denotes a channel, sl denotes a slice, view denotes a view, and w(n) denotes a monotonically increasing function that can take a value of 0.0 to 1.0. w(n) needs not to start with a value of 0.0 at the start of n and needs not to end with a value of 1.0 at the end of n.

Next, the end control unit 86 of the image generation function 442 of the X-ray CT apparatus 1 or the image generation function 741 of the medical image processing apparatus 70 determines whether to repeat or end the reconstruction by the reconstruction unit 83 and controlling the processing (step S7). When it is determined to repeat the reconstruction for improving image quality by the reconstruction unit 83 (No at step S7), the end control unit 86 allows the reconstruction unit 83 to repeat the reconstruction for improving image quality (steps S4 to S6).

Furthermore, when it is determined to end the reconstruction (Yes at step S7), the end control unit 86 allows the reconstruction unit 83 to perform reconstruction for output, and the reconstruction unit 83 generates the reconstructed image data D5 by performing reconstruction on an initial range designated by a user without being limited to the range of reconstruction of the information D3 on missing data (step S8).

Next, the output unit 87 of the image generation function 442 of the X-ray CT apparatus 1 or the image generation function 741 of the medical image processing apparatus 70 outputs the final reconstructed image data D5, which has been generated by the reconstruction for output, as the reconstructed image data D8 and outputting the latest projection data D7, which is the basis thereof, as the projection data D9 (step S9).

The order of the processing in the flowchart described in FIG. 3 may be changed as long as the results are not substantially affected. Furthermore, the processing may be performed in parallel as long as the results are not substantially affected.

Step S1 illustrated in FIG. 3 is a step corresponding to the scan control function 441 of the X-ray CT apparatus 1. Step S1 is a step in which the processing circuitry 44 of the X-ray CT apparatus 1 reads the computer program corresponding to the scan control function 441 from the memory 41 and executes the read computer program, so that the scan control function 441 is implemented.

Steps S2 to S9 are steps corresponding to the image generation function 442 of the X-ray CT apparatus 1 or the image generation function 741 of the medical image processing apparatus 70. Steps S2 to S9 are steps in which the processing circuitry 44 of the X-ray CT apparatus 1 or the processing circuitry 74 of the medical image processing apparatus 70 reads the computer program corresponding to the image generation function 442 or the image generation function 741 from the memory 41 or the memory 71 and executes the read computer program, so that the image generation function 442 or the image generation function 741 is implemented.

The processing circuitry 44 of the X-ray CT apparatus 1 or the processing circuitry 74 of the medical image processing apparatus 70 may perform switching, in accordance with the size of a region configured with at least one piece of missing data and the number of times that the region is repeatedly appears in the view direction, between whether to perform processing at Steps S3 to S8 described above, and whether to perform interpolation of the missing data with respect to the projection data D1, generate projection data D10 after the interpolation, and perform processing for generating reconstructed image data D11 from the projection data D10. Details of such a modification example will be described.

In the description of the modification example, the region configured with at least one piece of missing data includes a region configured with one piece of missing data and a region configured with continuous two or more adjacent pieces of missing data.

Figure 6:
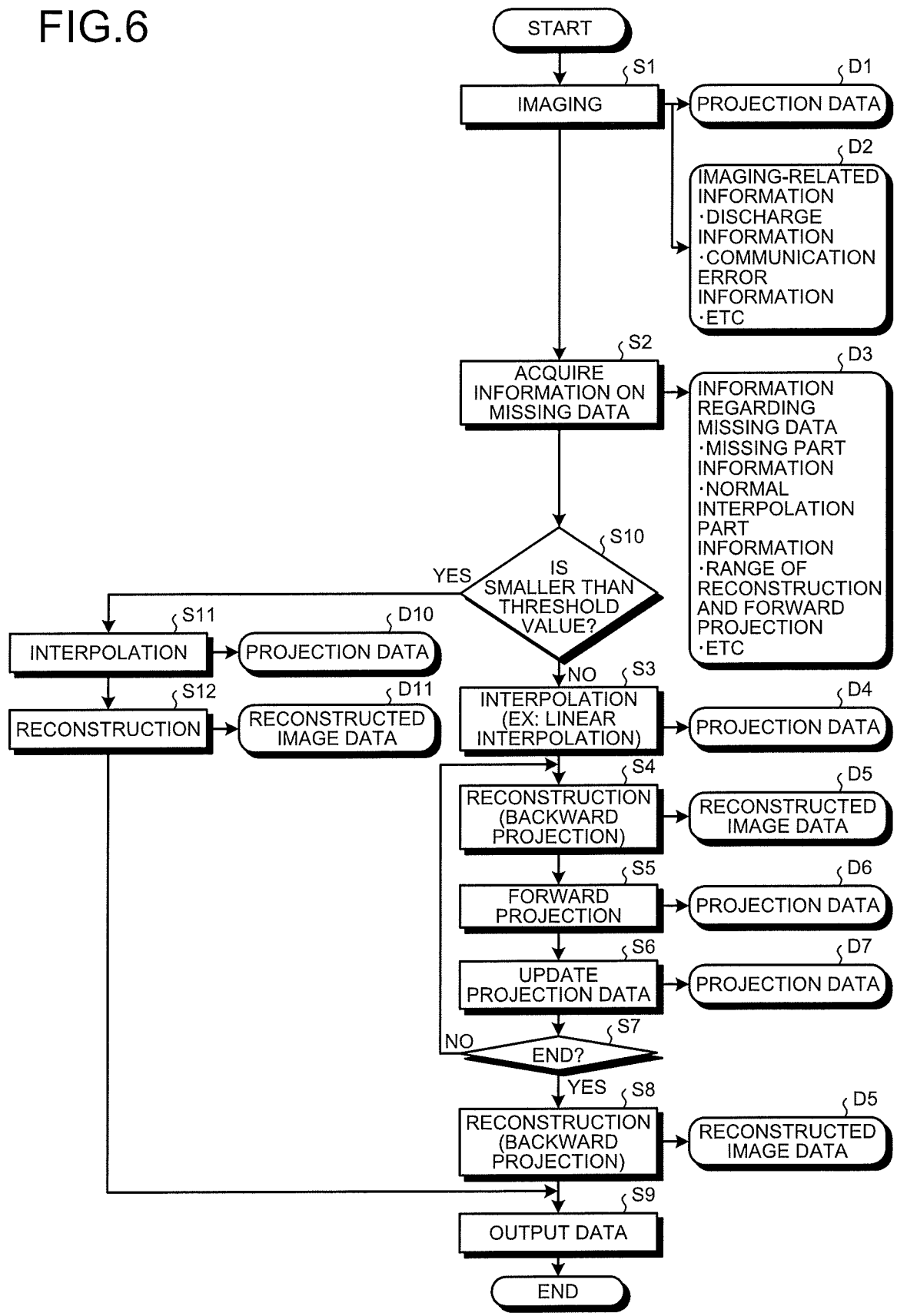
FIG. 6 is a flowchart illustrating a processing example according to an alternate embodiment.

FIG. 6 is a flowchart illustrating a processing example of the modification example of the embodiment. In the flowchart in FIG. 6, the same processing as that in FIG. 3 is given the same symbols as those in FIG. 3 and the description therefor is omitted.

As illustrated in FIG. 6, based on the missing part information of the information D3 on missing data, the generation unit 82 determines the size of a region configured with at least one piece of missing data, and determines whether the number of times that the region repeatedly appears in the view direction is smaller than a threshold value, in the projection data D1 (Step S10).

A specific example of determination at Step S10 will be described. For example, the generation unit 82 specifies, based on the missing part information of the information D3 on missing data, the size of the region configured with at least one piece of missing data. Furthermore, the generation unit 82 specifies, based on the missing part information of the information D3 on missing data, the number of times that the region repeatedly appears in the view direction.

Figure 7A:
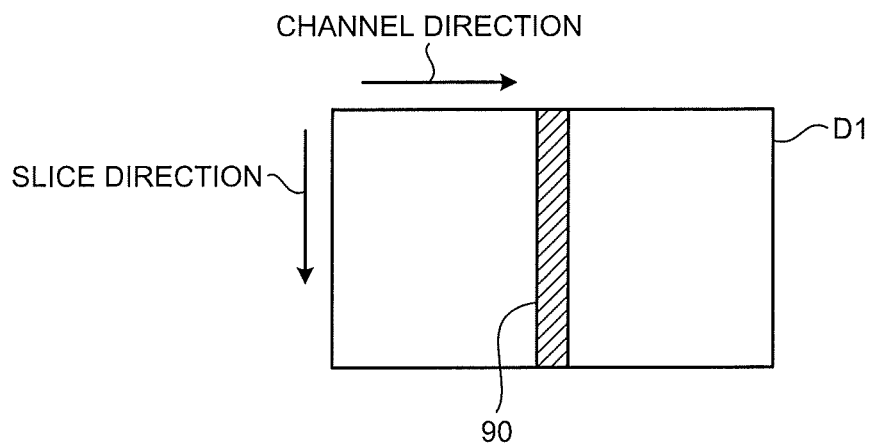
FIG. 7A is a diagram illustrating an alternate embodiment in which a region is configured with only one piece of missing data present in the channel direction and continuous adjacent pieces of missing data in the slice direction.

FIG. 7A is a diagram illustrating a modification example of the embodiment. FIG. 7A illustrates a region 90 configured with only one piece of missing data present in the channel direction and continuous eighty adjacent pieces of missing data in the slice direction, in the projection data D1. In this modification example, the description is made with a case in which the number of times that the region 90 is repeated in the view direction is "1000" as an example.

In FIG. 7A, the generation unit 82 specifies, as the size of the region 90 that is configured with continuous adjacent pieces of missing data, the largest number "1" that missing data is present in the channel direction within the region 90, and the largest number "80" that pieces of missing data continue in the slice direction within the region 90. Furthermore, the generation unit 82 specifies the number "1000" that the region 90 is repeated in the view direction.

The generation unit 82 determines whether a function min(ch_number,sl_number,view_number) is smaller than a predetermined threshold value α. The "ch_number" is the largest number of pieces of missing data continued in the channel direction within the region 90. The "sl_number" is the largest number of pieces of missing data continued in the slice direction within the region 90. When only one piece of missing data is present in each of the channel direction and the slice direction, the largest number of pieces of missing data continued is "1". The "view_number" is the number of times that the region 90 is repeatedly appears in the view direction. The function min(ch_number, sl_number, view_number) represents the minimum value out of the "ch_number", the "sl_number", and the "view_number". That is, in FIG. 7A, "min(1,80,1000)=1".

The predetermined threshold value α is a value obtained, for example, in a case where a user can accept deterioration of image quality after interpolation, by adding "1" to a maximum value among the largest number of pieces of missing data continued in the channel direction, the largest number of pieces of missing data continued in the slice direction, and the largest number of pieces of missing data continued in the view direction.

The generation unit 82 thus specifies a minimum value among the largest number of pieces of missing data continued in the channel direction within the predetermined region 90, the largest number of pieces of missing data continued in the slice direction within the predetermined region 90, and the number of times that the region 90 is repeatedly appears in the view direction. The generation unit 82 determines whether the specified minimum value is smaller than the predetermined threshold value α. The predetermined threshold value α is "2", for example.

When the specified minimum value is smaller than the predetermined threshold value α (Yes at Step S10), the missing data within the region 90 can be processed with interpolation. Thus, when the specified minimum value is smaller than the predetermined threshold value α (Yes at Step S10), the generation unit 82 performs, based on the missing part information of the information D3 on missing data and the normal interpolation part information, interpolation of the missing data part with respect to the projection data D1, and generates the projection data D10 after the interpolation (Step S11). The projection data D10 is an example of fifth projection data.

In FIG. 7A, for example, at Step S11, interpolation is performed for the missing data part with respect to the projection data D1 by using normal data adjacent with respect to the region 90 in the channel direction, and the projection data D10 after the interpolation is generated.

Figure 7B:
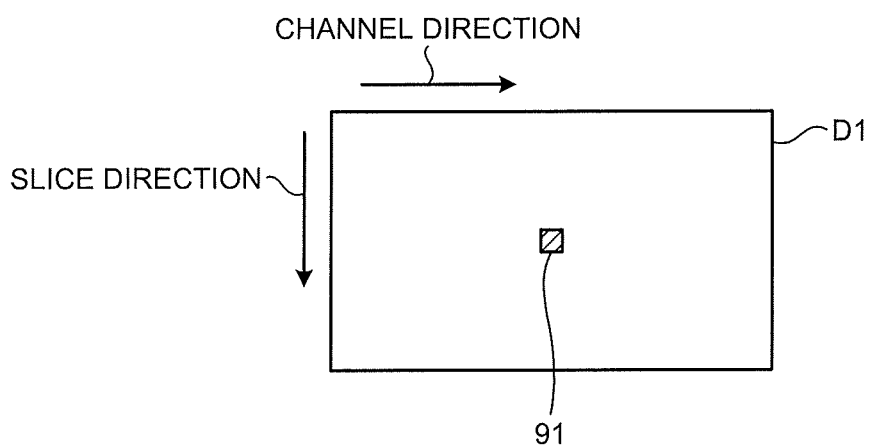
FIG. 7B is a diagram illustrating an alternate embodiment in which a region is configured with one piece of missing data present in the channel direction and one piece of missing data present in the slice direction.

With reference to FIG. 7B, another example of processing at Step S11 will be described. FIG. 7B is a diagram illustrating a modification example of the embodiment. FIG. 7B illustrates a region 91 configured with one piece of missing data present in the channel direction and one piece of missing data present in the slice direction, in the projection data D1. In this modification example, the description is made with a case in which the number of times that the region 91 is repeated in the view direction is "1000" as an example.

In FIG. 7B, "min(1,1,1000)" is smaller than the predetermined threshold value α. Thus, at Step S11, the generation unit 82 performs interpolation of missing data part with respect to the projection data D1, by using normal data adjacent with respect to the region 91 in the channel direction and normal data adjacent with respect to the region 91 in the slice direction, and generates the projection data D10 after the interpolation.

Next, the reconstruction unit 83 of the image generation function 442 of the X-ray CT apparatus 1 or the image generation function 741 of the medical image processing apparatus 70 generates the reconstructed image data D11 by performing reconstruction (backward projection) from the projection data D10 based on the range of reconstruction of the information D3 on missing data (step S12). The reconstructed image data D11 is an example of a third reconstructed image.

Next, at Step S9, the output unit 87 of the image generation function 442 of the X-ray CT apparatus 1 or the image generation function 741 of the medical image processing apparatus 70 outputs the final reconstructed image data D11, which has been generated by the reconstruction for output, and outputs the latest projection data D10, which is the basis thereof.

Figure 7C:
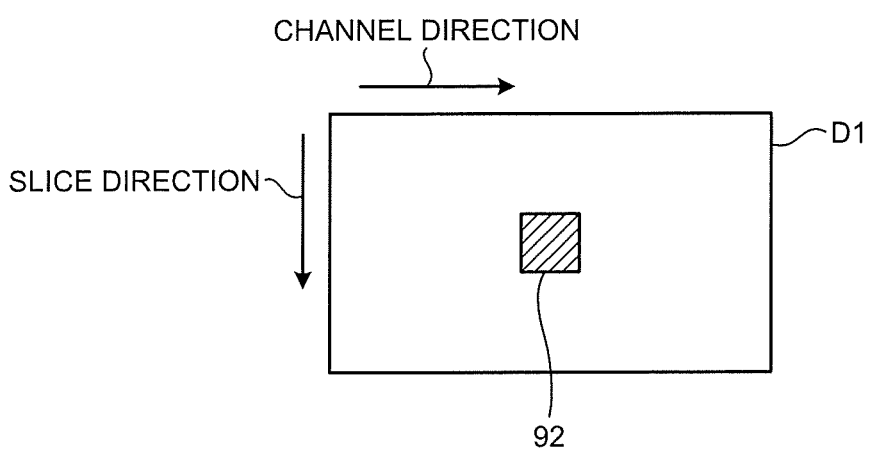
FIG. 7C is a diagram illustrating an alternate embodiment in which a region is configured with three pieces of continuous adjacent missing data in the channel direction and three pieces of continuous adjacent missing data in the slice direction.

With reference to FIG. 7C, an example of the process of determination at Step S10 will be described. FIG. 7C is a diagram illustrating a modification example of the embodiment. FIG. 7C illustrates a region 92 configured with continuous adjacent three pieces of missing data in the channel direction and continuous adjacent three pieces of missing data in the slice direction, in the projection data D1. In this modification example, the description is made with a case in which the number of times that the region 92 is repeated in the view direction is "1000" as an example.

In FIG. 7C, "min(3,3,1000)" is greater than the predetermined threshold value α. Thus, at Step S3, the generation unit 82 performs processing for generating the projection data D4. Next, at Step S4, the reconstruction unit 83 performs processing for generating the reconstructed image data D5. Then, at Step S5, the generation unit 84 performs processing for generating the projection data D6.

At Step S6, the projection data update unit 85 generates the projection data D7. After that, at Step S7, when the end control unit 86 determined that the reconstruction ends (Yes at Step S7), the reconstruction unit 83 performs processing for generating the reconstructed image data D5 at Step S8.

Next, at Step S9, the output unit 87 outputs the final reconstructed image data D5, which has been generated by the reconstruction for output, as the reconstructed image data D8 and outputs the latest projection data D7, which is the basis thereof, as the projection data D9.

As described above, the processing circuitry 44 of the X-ray CT apparatus 1 or the processing circuitry 74 of the medical image processing apparatus 70 performs switching, in accordance with the size of a region configured with at least one piece of missing data and the number of times that the region is repeatedly appears in the view direction, between whether to perform processing at Steps S3 to S8 described above, and whether to perform processing for generating projection data D10 after interpolation and generating reconstructed image data D11 from the projection data D10.

According to the present modification, the processing circuitry 44 or the processing circuitry 74 determines, at Step S10, whether it is possible to perform interpolation. A case where "it is possible to perform interpolation" is a case where a user can accept degradation of image quality after interpolation. When it is possible to perform interpolation, the processing circuitry 44 or the processing circuitry 74 performs, instead of processing at Steps S3 to S8, processing at Steps S10 to S12 that provide lower processing load compared with the processing load at Steps S3 to S8, and generates the reconstructed image data D11. Thus, according to the modification, compared with the above-described embodiment, it is possible to reduce the processing load.

According to at least one embodiment and the modification described above, it is possible to improve the image quality of a reconstructed image due to a data loss in projection data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical image processing apparatus comprising:
    processing circuitry configured to
        acquire information on missing data based on first projection data obtained by scanning a subject, generate second projection data by interpolating missing data in the first projection data based on the information on missing data, generate a first reconstructed image by reconstructing the second projection data, generate third projection data by performing forward projection on the first reconstructed image, generate fourth projection data by performing a weighted combination of the second projection data and the third projection data, and generate a second reconstructed image based on the fourth projection data.

2. The medical image processing apparatus according to claim 1, wherein the processing circuitry specifies, based on the information on missing data, a range for reconstructing the second projection data, and generates the first reconstructed image based on the specified range.

3. The medical image processing apparatus according to claim 1, wherein the processing circuitry specifies a range in which the first reconstructed image is forward-projected, based on the information on missing data, and generates the third projection data based on the specified range.

4. The medical image processing apparatus according to claim 1, wherein the information on missing data is based on discharge of an X-ray tube apparatus, failure of an X-ray detector, or a communication error between a data acquisition system and processing circuitry on a console device side.

5. The medical image processing apparatus according to claim 1, wherein the processing circuitry repeatedly performs processing for generating the third projection data, and processing for generating the fourth projection data.

6. The medical image processing apparatus according to claim 5, wherein the processing circuitry performs the processing for generating the third projection data, and the processing for generating the fourth projection data a predetermined number of times or until processing results are converged.

7. The medical image processing apparatus according to claim 1, wherein the processing circuitry performs switching, based on size of a region configured with at least one piece of missing data and a number of times that the region repeatedly appears in a view direction, between processing for generating the second projection data, processing for generating the first reconstructed image data, processing for generating the third projection data, and processing for generating the fourth projection data, and processing for generating fifth projection data by interpolating missing data in the first projection data based on the information on missing data and processing for generating a third reconstructed image by reconstructing the fifth projection data.

8. The medical image processing apparatus according to claim 1, wherein the processing circuitry configured to generate the fourth projection data by performing the weighted combination of the second projection data and the third projection data comprises processing circuitry configured to iteratively generate, for plural iterations, the fourth projection data by performing a weighted combination of (a) the second projection data multiplied by a scaling factor that decreases with each of the plural iterations and (b) the third projection data, and wherein the processing circuitry configured to generate the second reconstructed image based on the iteratively generated fourth projection data.

9. An X-ray CT apparatus comprising:

processing circuitry configured to acquire information on missing data based on first projection data obtained by scanning a subject, generate second projection data by interpolating the missing data in the first projection data based on the information on missing data, generate a first reconstructed image by reconstructing the second projection data, generate third projection data by performing forward projection on the first reconstructed image, generate fourth projection data by performing a weighted combination pf the second projection data and the third projection data, and generate a second reconstructed image based on the fourth projection data.

10. The X-ray CT apparatus according to claim 9, wherein the processing circuitry specifies, based on the information on missing data, a range for reconstructing the second projection data, and generates the first reconstructed image based on the specified range.

11. The X-ray CT apparatus according to claim 9, wherein the processing circuitry specifies a range in which the first reconstructed image is forward-projected, based on the information on missing data, and generates the third projection data based on the specified range.

12. The X-ray CT apparatus according to claim 9, wherein the information on missing data is based on discharge of an X-ray tube apparatus, failure of an X-ray detector, or a communication error between a data acquisition system and processing circuitry on a console device side.

13. The X-ray CT apparatus according to claim 9, wherein the processing circuitry repeatedly performs processing for generating the third projection data, and processing for generating the fourth projection data.

14. The X-ray CT apparatus according to claim 13, wherein the processing circuitry performs the processing for generating the third projection data, and the processing for generating the fourth projection data a predetermined number of times or until processing results are converged.

15. The X-ray CT apparatus according to claim 9, wherein the processing circuitry performs switching, based on size of a region configured with at least one piece of missing data and a number of times that the region repeatedly appears in a view direction, between processing for generating the second projection data, processing for generating the first reconstructed image data, processing for generating the third projection data, and processing for generating the fourth projection data, and processing for generating fifth projection data by interpolating missing data in the first projection data based on the information on missing data and processing for generating a third reconstructed image by reconstructing the fifth projection data.

16. The X-ray apparatus according to claim 9, wherein the processing circuitry configured to generate the fourth projection data by performing the weighted combination of the second projection data and the third projection data comprises processing circuitry configured to iteratively generate, for plural iterations, the fourth projection data by performing a weighted combination of (a) the second projection data multiplied by a scaling factor that decreases with each of the plural iterations and (b) the third projection data, and wherein the processing circuitry configured to generate the second reconstructed image based on the iteratively generated fourth projection data.

* * * * *